US009737017B1

(12) United States Patent
West et al.

(10) Patent No.: US 9,737,017 B1
(45) Date of Patent: Aug. 22, 2017

(54) INBRED CORN LINE KCNI 330

(71) Applicant: Kraft Foods Group Brands LLC, Chicago, IL (US)

(72) Inventors: Megan E. West, Palatine, IL (US); Harold Aycock, Greenfield, CA (US)

(73) Assignee: KRAFT FOODS GROUP BRANDS LLC, Chicago, IL (US)

( * ) Notice: Subject to any disclaimer, the term of this patent is extended or adjusted under 35 U.S.C. 154(b) by 0 days.

(21) Appl. No.: 15/085,246

(22) Filed: Mar. 30, 2016

(51) Int. Cl.
*A01H 5/10* (2006.01)
*C12N 15/82* (2006.01)
*A01H 1/02* (2006.01)

(52) U.S. Cl.
CPC ............... *A01H 5/10* (2013.01); *A01H 1/02* (2013.01); *C12N 15/825* (2013.01); *C12N 15/8274* (2013.01); *C12N 15/8281* (2013.01); *C12N 15/8282* (2013.01); *C12N 15/8283* (2013.01); *C12N 15/8286* (2013.01); *C12N 15/8289* (2013.01)

(58) Field of Classification Search
CPC ........................................................ A01H 5/10
USPC ...................................................... 800/320.1
See application file for complete search history.

(56) References Cited

U.S. PATENT DOCUMENTS

| | | | |
|---|---|---|---|
| 5,731,503 A | 3/1998 | Krier | |
| 6,008,437 A | 12/1999 | Krebbers et al. | |
| 6,506,964 B1 | 1/2003 | Carolo | |
| 8,053,634 B2 | 11/2011 | Tanaka et al. | |
| 8,153,866 B2 | 4/2012 | French | |
| 8,785,750 B2 * | 7/2014 | Stelpflug | C11B 1/00 426/655 |
| 2010/0297318 A1 | 11/2010 | Bottega | |
| 2012/0036592 A1 | 2/2012 | Bottega | |

FOREIGN PATENT DOCUMENTS

| | | |
|---|---|---|
| CN | 101663995 A | 3/2010 |
| EP | 1947179 B1 | 9/2011 |
| WO | 2008128761 A2 | 10/2008 |

OTHER PUBLICATIONS

Moreno et al., "Characterization of Anthocyanin Extracts from Maize Kernels", Journal of Chromatographic Science, vol. 43, pp. 483-487 (Oct. 2005).
Zhao et al., "Composition and Thermal Stability of Anthocyanins from Chinese Purple Corn (*Zea mays* L.)", Journal of Agricultural and Food Chemistry, 56, pp. 10761-10766 (Oct. 25, 2008).
Zhao et al., "Composition, antimicrobial activity, and antiproliferative capacity of anthocyanin extracts of purple corn (*Zea mays* L) from China", European Food Research and Technology, vol. 228, Issue 5, Abstract (Mar. 2009).
Minton, Barbara L., "Business Opportunity: Demand for Purple Corn May Soon Explode", <http://www.naturalnews.com/026210_corn_purple_cancer.html> (May 6, 2009).
Shipp et al., "Food Applications and Physiological Effects of Anthocyanins as Functional Food Ingredients", The Open Food Science Journal, 4, pp. 7-22 (2010).
Shivraj et al., "Antioxidant, α-Glucosidase and Xanthine Oxidase Inhibitory Activity of Bioactive Compounds From Maize (*Zea mays* L.)", Chemical Biology & Drug Design, 83: 119-125 (Oct. 4, 2013) DOI: 10.1111/cbdd.12205.
Nielsen, R.L. (Bob)., "Reddish-Purple Corn Plants Late in the Season," Purdue University Department of Agronomy (2009) <URL: http://www.kingcorn.org/news/timeless/PurpleCorn2.html> pp. 1-2.
Aoki, H., Noriko, K., Yoshiaki, K., Anthocyanins Isolated from Purple Corn (*Zea mays* L.), (2001) The Japan Food Chemical Research Foundation [online] <URL: http://www.ffcr.or.jp/zaidan/ffcrhome.nsf/7bd44c20b0dc562649256502001b65e9/1fbf0076d2b0a12949256a17001de57a/$FILE/199-6.pdf > pp. 1-10.

* cited by examiner

*Primary Examiner* — Li Zheng
(74) *Attorney, Agent, or Firm* — Dinsmore & Shohl LLP

(57) ABSTRACT

An inbred corn line, designated KCNI 330; the plants, seeds, and tissue cultures of the inbred corn line KCNI 330; methods for producing a corn plant, either inbred or hybrid, by crossing a plant of the inbred corn line KCNI 330 with itself or another corn plant of a different genotype; and hybrid corn seeds and plants produced by crossing a plant of the inbred corn line KCNI 330 with a corn plant of a different genotype.

20 Claims, 2 Drawing Sheets

INBRED CORN LINE KCNI 330

TECHNICAL FIELD

The present specification generally relates to the field of corn breeding, specifically, the plants and plant parts, including seeds, of the inbred corn line designated KCNI 330, and inbred corn lines, hybrid corn varieties, and tissue cultures derived therefrom.

BACKGROUND

Corn (*Zea mays* L.) is grown widely in the United States and has been the subject of breeding programs and human manipulation for centuries. Corn is a monoecious plant, meaning one plant has both male and female flowers. The male flower is located in the tassel at the top of the corn plant and produces pollen. The female flower is located in the ear shoot on the stalk of the corn plant and receives pollen from the male flower. Thus, corn is capable of self-pollination (pollen from the male flower is received by the female flower of the same plant) or is capable of cross-pollination (pollen from the male flower is received by the female flower of a different plant). Sib-pollination occurs when the female flower of one corn plant receives pollen from the male flower of another corn plant of the same line.

Inbred lines are developed by allowing or directing a plant to self-pollinate or sib-pollinate for a number of generations. After each generation, plants with a desired trait or a combination of desired traits are selected and allowed to self-pollinate or sib-pollinate again. The process is repeated until the population is homozygous and true breeding for that trait or combination of traits. Usually, inbred corn lines are developed so that they can then be crossed with a different inbred corn line to create new hybrid corn varieties. Due to a phenomenon known as hybrid vigor, inbred corn lines are typically not as vigorous or high yielding as hybrid corn varieties. Thus, the plants of the hybrid corn varieties typically exhibit better agronomic characteristics than the plants of the parent inbred corn lines.

SUMMARY

In one embodiment, a plant of the inbred corn line KCNI 330 is provided. In another embodiment, a seed of the inbred corn line KCNI 330 is provided. Plants of the inbred corn line KCNI 330 produce higher concentrations of anthocyanins than most other corn varieties.

In another embodiment, other parts of the plants of the inbred corn line KCNI 330 are also provided, including, for example, pollen grains, protoplasts, cells, tassels, anthers, or ovules. In one embodiment, a tissue culture of regenerable cells produced from a plant of the inbred corn line KCNI 330 and a plant regenerated from the tissue culture are also provided.

In yet another embodiment, a method of producing a progeny plant derived from a plant of the inbred corn line KCNI 330 includes crossing the plant of the inbred corn line KCNI 330 with a plant of a different genotype to produce at least a first seed. In another embodiment, the method further includes crossing a plant grown from the first seed with itself or a plant of a different genotype to produce a seed of a progeny plant; (b) growing the progeny plant from the seed of the progeny plant and crossing the progeny plant with itself or a plant of a different genotype; and (c) repeating steps (a) and (b) until a seed of a plant derived from the plant of the inbred corn line KCNI 330 is produced.

In another embodiment, a method of producing a progeny plant derived from the inbred corn line KCNI 330 includes crossing a plant of the inbred corn line KCNI 330 with a plant of a different genotype to produce at least a first seed. The plant of a different genotype has a desired trait. The method further includes (a) crossing a plant grown from the first seed with itself or a plant of a different genotype to produce progeny plants, wherein at least some of the progeny plants have the desired trait; (b) selecting the progeny plants that have the desired trait; (c) crossing the selected progeny plants with the plant of the inbred corn line KCNI 330 to produce backcross progeny plants, wherein at least some of the backcross progeny plants have the desired trait; (d) selecting for the backcross progeny plants that have the desired trait; and (e) repeating steps (c) and (d) until a seed of a plant derived from the plant of the inbred corn line KCNI 330 having the desired trait is produced.

These and additional features provided by the embodiments described herein will be more fully understood in view of the following detailed description.

BRIEF DESCRIPTION OF THE DRAWINGS

The embodiments set forth in the drawings are illustrative and exemplary in nature and not intended to limit the subject matter defined by the claims. The following detailed description of the illustrative embodiments can be understood when read in conjunction with the following drawings, in which:

DETAILED DESCRIPTION

Figure 1:
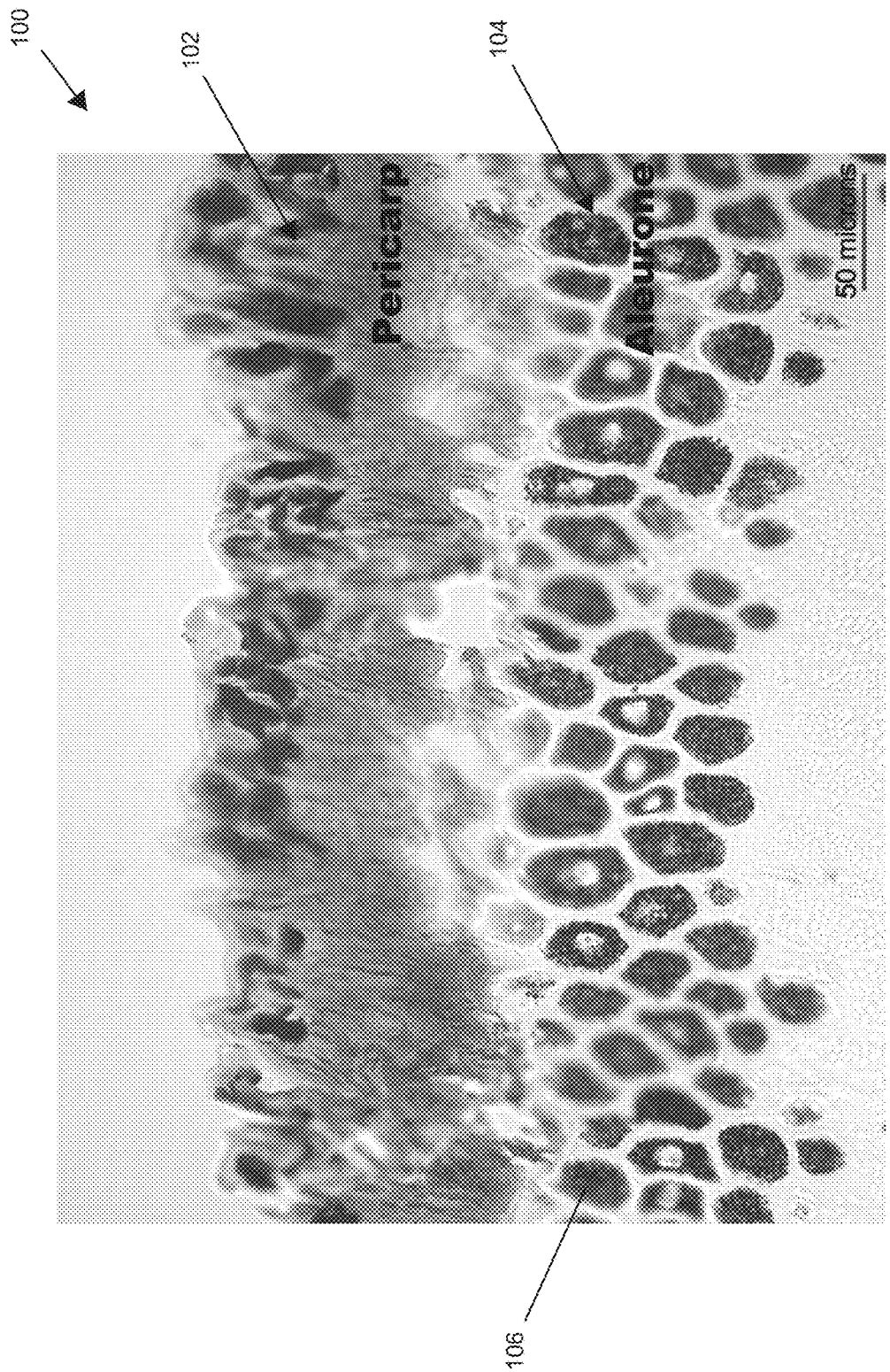
FIG. 1 depicts a cross-sectional view of a kernel of a plant of inbred corn line KCNI 330 obtained by microscopy.

Corn breeding programs may be designed to foster certain desired traits in a specific inbred corn line or subsequent hybrid corn varieties. These traits may enhance the general performance of the plant, including traits such as greater yield, stronger stalks, or stronger roots; boost survival in a specific environment, including traits such as drought resistance, disease resistance, or pest resistance; and/or promote the production of certain industry-specific characteristics or products, including traits such as increased mineral and vitamin content, increased oil production, or waxy starch. The list of desired traits is long and oftentimes industry and location specific.

Corn breeding programs may also be designed to develop hybrid corn varieties based on stable inbred corn lines that consistently exhibit a desired trait or a set of desired traits. This can be a long and costly process. Once a desired trait or set of desired traits are identified, the process of selecting at least two different corn lines to serve as parent plants and cultivating those corn lines begins. First, at least two different parent plants, at least one of which exhibits a desired trait, are selected. Then, each of the parent plants are allowed to self-pollinate or sib-pollinate until each produces a population that is sufficiently homozygous and true breeding, thereby creating two inbred corn lines. Then, plants of the at least two parent corn lines are crossed to produce plants of a first generation, which are further evaluated to determine the presence of the desired trait(s). If the desired trait is not present, the process may restart with new parent plants. The development of these inbred corn lines that serve as parent plants to subsequent hybrid corn varieties is fundamental to any breeding program and requires close attention to industry needs and trends. Accordingly, there is a need for new, stable inbred corn lines that exhibit desired traits useful for a variety of industry and agricultural operations.

I. Inbred Corn Line KCNI 330

In one embodiment, the plant and plant parts, including seeds, of the inbred corn line KCNI 330 are provided. The inbred corn line KCNI 330 is a new line that has floury endosperm and increased concentrations of anthocyanins in the kernels. The inbred corn line KCNI 330 was developed from an initial cross in 2004 of a single plant (later designated 04 GF 967-1) that was grown from about sixty dark red segregating kernels planted from a single ear of colored ornamental corn purchased in the local area and pollinated with pollen from a proprietary floury endosperm inbred corn line CNI 0103. Some of the about sixty plants grown from that seed were self-pollinated and some were crossed with proprietary inbred lines having floury endosperm. Forty of those plants were planted in the 2004-2005 Chile Winter Nursery for self-pollination. The mature self-pollinated ears were harvested and dried. Ten ears were selected and shelled individually for further inbreeding and selection and some were then crossed with other corn lines to test agronomic performance as a hybrid. Inbred corn line KCNI 330 was derived from one of those ten selected ears and ten generations of inbreeding while selecting for the dark purple kernel color and agronomic fitness using the ear to row method and relatively strong agronomic performance in hybrid combinations. The seed of a selected ear from an individual self-pollinated plant in the tenth generation of inbreeding became the foundation seed source for increasing seed stocks of inbred corn line KCNI 330. Thus, through selection and subsequent rounds of inbreeding, the inbred corn line KCNI 330 was developed.

The plants of the inbred corn line KCNI 330 produce increased concentrations of anthocyanins compared to most other corn varieties, exhibit agronomic fitness, and can be used to make single-cross hybrid corn varieties of plants that also produce increased concentrations of anthocyanins. The plant tissue of the inbred corn line KCNI 330 exhibits a purple color due to the presence of anthocyanins in the plant tissue. In some embodiments, the kernels of the plants of the inbred corn line KCNI 330 have the highest concentrations of anthocyanins in the plant. In particular, the aleurone and pericarp tissue of the kernel contains high concentrations of anthocyanins.

Anthocyanins belong to a class of organic compounds known as flavonoids. They are water-soluble glycosides of polyhydroxy and polymethoxy derivatives of 2-phenylbenzopyrylium or flavylium salts. Anthocyanins are secondary metabolites produced by plants. Anthocyanins exhibit a red, blue, or purple color depending on the pH. They are a natural product with many health benefits and are particularly desired for application in the food and beverage industry. (e.g., Shipp and Abdel-Aal, *Open Food Science J.*, 4:7-22 (2010)).

Referring now to FIG. 1, a portion of a section 100 of the pericarp tissue 102 and the aleurone tissue 104 of a kernel of a plant of the inbred corn line KCNI 330 is viewed under a light microscope. To obtain such a sample, a kernel of a plant of inbred corn line KCNI 330 is first sectioned at 300-400 microns using a rotary microtome. The section 100 is then transferred to a drop of mineral oil on a slide and examined under a light microscope in Differential Interference Contrast phase at 20×. The darker regions 106 in the section 1400 show the distribution and color of the anthocyanins present in the pericarp tissue 102 and the aleurone tissue 104 of the kernel of a plant of the inbred corn line KCNI 330.

A description of the physical and morphological characteristics of inbred corn line KCNI 330 is provided in Table 1.

TABLE 1

Physical and Morphological Characteristics for Inbred Corn Line KCNI 330

| Characteristics | Average Value |
|---|---|
| TYPE | |
| 1 = Sweet, 2 = Dent, 3 = Flint, 4 = Flour 5 = Pop, 6 = Ornamental, 7 = Pipecorn, 8 = Other | 4 |
| MATURITY | |
| Days from emergency to 50% plants in silk | 64 days |
| Days from emergence to 50% of plants in pollen. | 66 days |
| Days from 10% to 90% pollen shed | 10 days |
| Days from 50% silk to harvest at 25% moisture | 60 days |
| PLANT | |
| Plant height (cm) | 156.7 cm |
| Ear height (cm) | 54.0 cm |
| Length of top ear internode (cm) | 12.1 cm |
| Average number of tillers | 0.1 |
| Average number of ears per stalk | 1.5 |
| Anthocyanin of brace roots | Dark |
| LEAF | |
| Width of ear node leaf (cm) | 8.4 cm |
| Length of ear node leaf (cm) | 77.9 cm |
| Number of leaves above top ear | 5 |
| Leaf angle degrees (from $2^{nd}$ leave above ear at anthesis to stalk above leaf) | 33.8 degrees |
| Leaf color | Medium Green (Munsell code 7.5GY 4/6) |
| Leaf sheath pubescence (rate on scale from 1 = none to 9 = like peach fuzz) | 4 |
| Marginal waves (rate on a scale from 1 = none to 9 = many) | 3 |
| Longitudinal creases (rate on scale from 1 = none to 9 = many) | 5 |
| TASSEL | |
| Number of primary lateral branches | 12 |
| Branch angle from central spike | 32.4 |
| Tassel length (cm) | 33.7 cm |
| Pollen shed (rate on scale from 0 = male sterile to 9 = heavy shed) | 7 |
| Anther color | Purple (Munsell Code 5RP 4/10) |
| Glume color | Medium Green (Munsell Code 2.5G 5/6) |
| Bar glumes | Present |
| EAR (UNHUSKED) | |
| Silk color (3 days after emergence) | Purple (Munsell Code 5RP 3/6) |
| Fresh husk color (25 days after 50% silking) | Purple (Munsell Code 5RP 3/2) |
| Dry husk color (65 days after 50% silking) | Purple (Munsell code 5RP 4/2) |
| Position of ear at dry husk stage: | Horizontal |
| Husk extension (at harvest): | Medium (<8 cm) |
| EAR (HUSKED) | |
| Ear length (cm) | 9.6 cm |
| Ear diameter at mid-point (mm) | 32.0 cm |
| Ear weight (gm) | 25.4 gm |
| Number of kernel rows | 12 |
| Kernel rows | Distinct |

TABLE 1-continued

Physical and Morphological Characteristics
for Inbred Corn Line KCNI 330

| Characteristics | Average Value |
|---|---|
| Row alignment | Slightly curved |
| Ear taper | Average |
| KERNEL | |
| Kernel length (mm) | 8.4 mm |
| Kernel width (mm) | 8.8 mm |
| Kernel thickness (mm) | 5.8 mm |
| % round kernels (shape grade) | 41.9% |
| Aleurone color pattern: | Homozygous |
| Aleurone color | Purple (Munsell Code 2.5R 4/2) |
| Hard endosperm color | Pale Purple (Munsell Code 2.5R 5/2) |
| Endosperm type | Waxy starch |
| Weight per 100 kernels (unsized sample) (gm) | 15.2 gm |
| COB | |
| Cob diameter at mid-point (mm) | 24.0 mm |
| Cob color | Purple (Munsell Code 5RP 3/2) |
| AGRONOMIC TRAITS | |
| Stay green (at 65 days after anthesis) (rate on a scale of 1 = worst to 9 = excellent) | 1 |
| % dropped ears (at 65 days after anthesis) | 0.0% |
| % pre-anthesis brittle | 0.0% |
| % pre-anthesis root lodging | 0.0% |
| % post-anthesis root lodging (at 65 days after anthesis) | 39.2% |
| Yield of inbred per se (at 12-13% grain moisture) (kg/ha) | 373.7 kg/ha |

Inbred corn line KCNI 330 was bred through a sufficient number of rounds of self-pollination to create a line that is homozygous and true breeding. Inbred corn line KCNI 330 shows uniformity within the limits of environmental influence for the traits described in Table 1 and no variant traits have been or are expected to be detected.

In another embodiment, parts of the plants of the inbred corn line KCNI 330 are also provided, including embryos, pollen, ovules, flowers, seeds, kernels, ears, cobs, leaves, husks, stalks, roots, root tips, brace roots, lateral tassel branches, anthers, tassels, glumes, silks, tillers, and the like. In yet another embodiment, cells, protoplasts, regenerable tissue cultures, DNA, calli, and clumps of the plants of the inbred corn line KCNI 330 are provided. These parts may be used to create tissue cultures that are capable of propagating plants of the inbred corn line KCNI 330 using a variety of techniques familiar to a person of skill in the art and discussed in further detail below.

The kernels and other parts of the plants of the inbred corn line KCNI 330 exhibit a purple color due to an increased concentration of anthocyanins present in the tissue. In some embodiments, the kernels of the plants of the inbred corn line KCNI 330 may include between 500 mg anthocyanins/kg of dry corn and 600 mg anthocyanins/kg of dry corn. In another embodiment, the kernels of the plants of the inbred corn line KCNI 330 may include between 500 mg anthocyanins/kg of dry corn and 550 mg anthocyanins/kg of dry corn. In yet another embodiment, the kernels of the plants of the inbred corn line KCNI 330 may include between 500 mg anthocyanins/kg of dry corn and 525 mg anthocyanins/kg of dry corn.

The plants of the inbred corn line KCNI 330 also include several different anthocyanin compounds. In some embodiments, the tissue of the plants of inbred corn line KCNI 330 has high concentrations of acylated anthocyanin compounds. As examples and not limitations, the anthocyanins present in the kernels of a plant of inbred corn line KCNI 330 may include catechin-(4,8)-cyanidin-3,5-diglucoside; catechin-(4,8)-cyanidin-3-malonylglucoside-5-glucoside; cyanidin 3-glucoside; pelargonidin 3-glucoside; peonidin 3-glucoside; cyanidin 3-(6"-malonyl)glucoside; pelargonidin 3-(malonyl)glucoside; and cyanidin 3-(malonyl)(malonyl)glucoside. Table 2 below shows the relative amount of each anthocyanin compound present in a sample of kernels from a plant of the inbred corn line KCNI 330.

TABLE 2

Relative Amount of Anthocyanins Present in a Sample of
Kernels from a Plant of the inbred Corn Line KCNI 330

| Anthocyanin Compound | Relative Amount |
|---|---|
| catechin-(4,8)-cyanidin-3,5-diglucoside | 2.37 |
| catechin-(4,8)-cyanidin-3-malonylglucoside-5-glucoside | 3.95 |
| cyanidin 3-glucoside | 12.46 |
| pelargonidin 3-glucoside | 2.00 |
| peonidin 3-glucoside | 7.49 |
| cyanidin 3-(6"-malonyl)glucoside | 26.88 |
| pelargonidin 3-(malonyl)glucoside | 6.00 |
| cyanidin 3-(malonyl)malonyl)glucoside | 23.45 |
| other anthocyanins | 15.40 |

Figure 2:
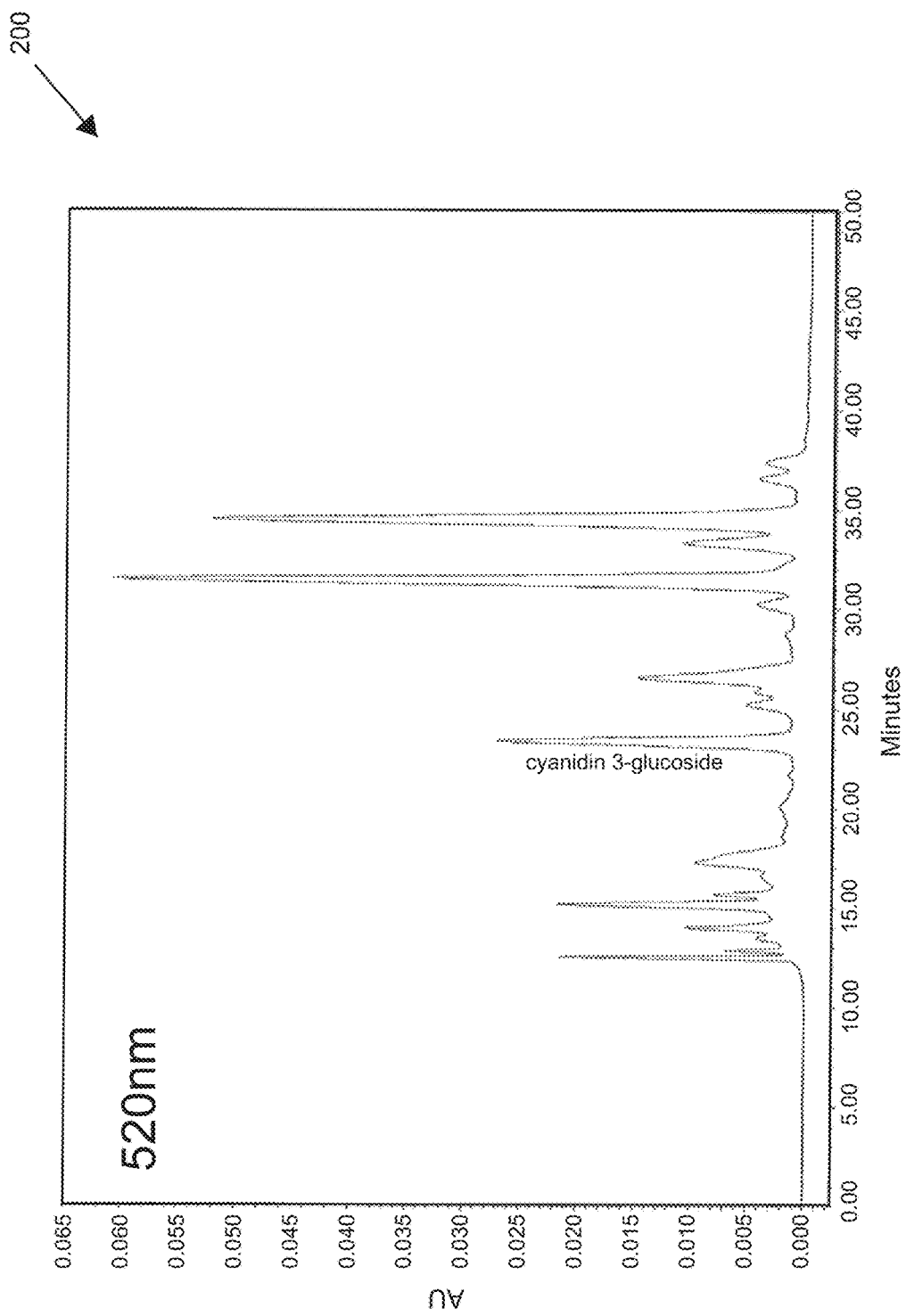
FIG. 2 depicts a chromatogram of a high performance liquid chromatography analysis of a sample of kernels of a plant of inbred corn line KCNI 330.

Referring now to FIG. 2, the relative amounts of anthocyanins present in the tissue of the kernels of a plant of the inbred corn line KCNI 330 can be determined through HPLC analysis, the results of which may be similar to those depicted in a chromatograph 200. As an example and not a limitation, the HPLC analysis may proceed as follows. First, a 2±0.1 g sample of kernels of the inbred corn line KCNI 330 is prepared. The kernels may be used whole or may be ground. The anthocyanins are then extracted from the sample using 10 mL of 2% formic acid overnight in a dark room at room temperature and under a blanket of argon. The extract is then filtered into a HPLC vial using a 0.45 μm Millipore Millex LCR filter. If the sample consists of ground kernels, the extract may be centrifuged before it is filtered. A 20 μL sample is then injected into a C18 5μ guard column (e.g., 7.5 mm×4.6 mm) and then into a C18 5μ analytical column (e.g., 250 mm×4.6 mm). The column oven is set to 30° C. The chromatography is done using a gradient mobile phase starting with 100% of a solvent of 2% formic acid in water and including an amount of up to 40% of a second solvent of acetonitrile or methanol over 35 or 50 minutes, respectively. The separate anthocyanins in the sample are detected at the exit of the analytical column using a PDA detector. From PDA detector data, the type of anthocyanin present in the sample and the relative amount of each type of anthocyanin can be determined using methods known to those of skill in the art.

Plants of the inbred corn line KCNI 330 can be reproduced by planting the seeds of the inbred corn line KCNI 330, allowing the plants to grow, and allowing or directing the plants to self-pollinate or sib-pollinate using techniques familiar to one skilled in the art. Eventually, the kernels and other parts of the plants of the inbred corn line KCNI 330 can be harvested using techniques familiar to one of skill in the art. The kernels and other parts of the plants of the inbred corn line KCNI 330 may be used in a variety of applications. In some embodiments, anthocyanins will be extracted from the kernels and other parts of the plants of the inbred corn line KCNI 330 for use in food and beverage applications as a natural colorant. For examples of available extraction techniques for anthocyanins, see, e.g., Zhao et al., *J. Ag. Food Chem.* 56:10761-66 (2008); Garcia-Salas et al., *Molecules*, 15:8813-26 (2010).

C. Deposit Information

A deposit of at least 2,500 seeds of the inbred corn line KCNI 330 was made with the American Type Culture Collection (ATCC), 10801 University Boulevard, Manassas, Va. 20110. The deposit is assigned ATCC Accession No. PTA-123287. The deposit was made on Jun. 24, 2016. Access to this deposit will be available during the pendency of the application to the Commissioner of Patents and Trademarks and persons determined by the Commissioner to be entitled thereto upon request. The deposit will be maintained with the ATCC Depository, which is a public depository, for a period of 30 years, or 5 years after the most recent request, or for the enforceable life of the patent, whichever is longer, and will be replaced if it becomes nonviable during that period. Applicant does not waive any infringement of their rights granted under this patent.

II. Development of Other Corn Lines Using Inbred Corn Line KCNI 330

A. Producing Hybrid Corn Varieties Using Inbred Corn Line KCNI 330

Plants of the inbred corn line KCNI 330 may also be used to produce plants of new corn lines or varieties, in particular, new hybrid corn varieties. In one embodiment, plants of the inbred corn line KCNI 330 are crossed with plants of another inbred corn line of a different genotype and then evaluated. When two inbred parent lines are crossed, the result is a uniform population of heterozygous F1 hybrid plants.

Hybrid varieties may be produced as a single-cross hybrid, a three-way hybrid, or a double-cross hybrid. A single-cross hybrid is produced from the cross of two inbred parent plants. A three-way hybrid involves plants of three inbred parent lines. Plants from the first two inbred parent lines are crossed to produce plants of a single-cross hybrid variety. Then, the plants of the single-cross hybrid variety are crossed with the plants of the third inbred parent line. A double-cross hybrid involves two sets of inbred corn lines, four lines in total. Plants of each set of inbred corn lines are crossed to produce two sets of single-cross hybrid corn varieties. Then, the plants of the two single-cross hybrid corn varieties are crossed with each other to produce plants of a double-cross hybrid corn variety. It should be understood that the plants of the inbred corn line KCNI 330 may be used in a variety of different crosses with plants of different inbred corn lines or hybrid corn varieties to produce plants of either single-cross, three-way cross, or double cross hybrid varieties.

When crossing two inbred parent lines, one line is designated as the female parent (the plant that receives pollen) and the other line is designated as the male parent (the plant that produces pollen). In some embodiments, plants of the inbred corn line KCNI 330 are designated as the female parent plants in a cross because the aleurone and pericarp tissue of a kernel in a plant is supplied by the female parent plant, and, as discussed above, the aleurone and pericarp tissue in the plants of the inbred corn line KCNI 330 contain the highest concentrations of anthocyanins. Thus, the plants of the inbred corn line KCNI 330 are designated as the female parent plant in a cross when it is desirable for the plants of the resulting hybrid corn varieties to have high concentrations of anthocyanins in the aleurone and pericarp tissue of the kernel.

Male sterility is often conferred on the line of plants designated as the female parent plant so that those plants cannot produce pollen, which helps to avoid inadvertent self-pollination or sib-pollination. Male sterility may be conferred through a variety of methods including manually or mechanically removing the tassel of the female parent plants, conferring male sterility through the use of genetic transformation, or applying gametocides. The male parent plant is typically destroyed or removed after pollination occurs so that its own self-pollinated kernels are not collected and mixed with the seed of the resulting hybrid corn variety.

In one embodiment, a method of developing a hybrid corn variety using the plants of the inbred corn line KCNI 330 includes first procuring or producing a plant having a different genotype from the plants of the inbred corn line KCNI 330. The plants of a different genotype may exhibit a desired trait or combination of desired traits. The plants of a different genotype are crossed with plants of the inbred corn line KCNI 330 to produce plants of a first generation hybrid corn variety, known as the F1 generation. The plants of the F1 generation may be evaluated for a defined set of criteria, including anthocyanin production and/or the presence of the desired trait(s). If the plants of the F1 generation meet the defined set of criteria, the cross that includes the plants of the inbred corn line KCNI 330 and the plants of a different genotype may be repeated indefinitely to yield the same F1 generation, resulting in a new hybrid corn variety.

In some embodiments, the plants of the hybrid corn varieties developed using plants of the inbred corn line KCNI 330 also have higher concentrations of anthocyanins than most other corn varieties. As an example and not a limitation, when the plants of the inbred corn line KCNI 330 are crossed with a plant of the inbred corn line designated CNI 17-3-1, a plant of a hybrid corn variety designated 12CH28 is formed. The inbred corn line CNI 17-3-1 is a proprietary inbred corn line that is a tall, vigorous line. In one embodiment, the kernels of the plants of the hybrid corn variety 12CH28 may include between 300 mg anthocyanins/kg of dry corn and 400 mg anthocyanins/kg of dry corn. In another embodiment, the kernels of the plants of the hybrid corn variety 12CH28 may include between 350 mg anthocyanins/kg of dry corn and 400 mg anthocyanins/kg of dry corn. In yet another embodiment, the kernels of the plants of the hybrid corn variety 12CH28 may include between 350 mg anthocyanins/kg of dry corn and 375 mg anthocyanins/kg of dry corn.

In another embodiment, the plants of the hybrid corn lines produced using plants of the inbred corn line KCNI 330 have higher concentrations of anthocyanins than most other corn varieties, one or more desired trait(s), and increased vigor. The desired trait(s) may include, but are not limited to: higher yield; better response to soil fertility; tolerance to extreme temperatures; resistance to drought; increased stalk quality; increased root quality; shorter time to crop maturity; resistance to insects and pests; tolerance and/or resistance to herbicides; resistance to viral diseases; resistance to bacterial diseases; resistance to fungal diseases; increased production of amino acids, minerals, vitamins, oils, or other compounds; improved dry and wet milling properties; male sterility; improved nutritional content; or the like. (e.g., Moose and Mumm, *Plant Physiology*, 147(3):969-77 (2008).)

B. Producing Inbred Corn Lines Using the Inbred Corn Line KCNI 330

Plants of the inbred corn line KCNI 330 may also be used to produce plants of new corn lines, in particular, new inbred corn lines. In one embodiment, the plants of the inbred corn line derived from the plants of the inbred corn line KCNI 330 have the physiological and morphological characteristics of KCNI 330. In yet another embodiment, the plants of the inbred corn line derived from the plants of the inbred corn line KCNI 330 have the physiological and morphological characteristics of KCNI 330 along with one or more desired trait(s). The desired trait(s) may include, but are not limited to: higher yield; better response to soil fertility; tolerance to extreme temperatures; resistance to drought; increased stalk quality; increased root quality; shorter time to crop maturity; resistance to insects and pests; tolerance and/or resistance to herbicides; resistance to viral diseases; resistance to bacterial diseases; resistance to fungal diseases; increased production of amino acids, minerals, vitamins, oils, or other compounds; improved dry and wet milling properties; male sterility; improved nutritional content; or the like. (e.g., Moose and Mumm, *Plant Physiology*, 147 (3):969-77 (2008).)

In one embodiment, a technique known as pedigree breeding is used to develop plants of an inbred corn line derived from the inbred corn line KCNI 330. This method includes crossing a plant of the inbred corn line KCNI 330 with a plant of a different genotype to produce a first generation, known as the F1 generation. The plant of a different genotype may exhibit a desired trait or combination of desired traits. The plants of the F1 generation are evaluated for a defined set of criteria, which may include higher anthocyanin concentrations in the tissue of the plants than other corn varieties and/or the presence of the desired trait(s).

The method further includes allowing or directing the plants of the F1 generation to self-pollinate or sib-pollinate to produce plants of another generation, known as plants of the F2 generation. The F2 generation is known as a segregating breeding population. The plants of the F1 generation are genetically identical because all of these plants are heterozygous, meaning they all have the same combination of alleles for every gene (one allele is from the homozygous male inbred parent and one allele is from the homozygous female inbred parent). In contrast, the plants of the F2 generation are genetically unique because the combination of the alleles in each plant may be different from that of another plant in the F2 generation.

The method further includes selecting plants of the F2 generation that exhibit the physiological and morphological characteristics of the plants of the inbred corn line KCNI 330 along with the desired trait(s) and then allowing or directing those plants to self-pollinate or sib-pollinate. This step may be repeated as many times as necessary to achieve a new inbred corn line derived from the plants of the inbred corn line KCNI 330. In some embodiments, the plants of the inbred corn line derived from the plants of the inbred corn line KCNI 330 exhibit the physiological and morphological characteristics of the plants of the inbred corn line KCNI 330 and the desired trait(s).

The complexity of this method and the number of times the steps of selecting plants based on whether they exhibit the physiological and morphological characteristics of the plants of the inbred corn line KCNI 330 along with the desired trait(s) and allowing or directing those plants to self-pollinate or sib-pollinate must be repeated varies depending on many factors, including the desired trait(s), the level of expression of the trait(s), the type of inheritance, and the plant of a different genotype used in the cross. In some embodiments, the method is repeated as many as three to ten times.

In yet another embodiment, a technique known as back-crossing is used to develop plants of a new inbred corn line derived from the inbred corn line KCNI 330. This method includes crossing plants of two different corn lines, one of which is known as the "donor parent" and one of which is known as the "recurrent parent." The donor parent plant is only used in the initial cross with the recurrent parent plant. Then, plants of subsequent generations are either allowed to self-pollinate or sib-pollinate or are crossed again with the recurrent parent.

In this embodiment, the method includes first crossing a plant of the inbred corn line KCNI 330 with a plant of a different genotype to produce plants of an F1 generation. The plant of a different genotype may exhibit a desired trait or a combination of desired traits. The plants of the F1 generation are then allowed to self-pollinate or sib-pollinate to produce plants of an F2 generation. As discussed above, the plants of the F2 generation are part of a segregated breeding population.

The method further includes selecting plants of the F2 generation that have the desired trait(s) and crossing the selected plants of the F2 generation with the plants of the inbred corn line KCNI 330, the recurrent parent, to create plants of a backcross progeny. The method may also include selecting plants from the backcross progeny that have the morphological and physiological characteristics of the plants of the inbred corn line KCNI 330 and the desired trait(s). This method may be repeated as many times as necessary to achieve a new inbred corn line that exhibits the morphological and physiological characteristics of the plants of the inbred corn line KCNI 330 and the desired trait(s).

The complexity of this method and the number of times the steps of selecting plants based on whether they exhibit the physiological and morphological characteristics of the plants of the inbred corn line KCNI 330 along with the desired trait(s) and crossing those selected plants with the recurrent parent plants of the inbred corn line KCNI 330 must be repeated varies depending on many factors, including the desired trait(s), the level of expression of the trait, the type of inheritance, and the other line used in the cross. In some embodiments, the method is repeated as many as three to ten times.

A person of ordinary skill in the art would appreciate the various means and methods for screening the plants of the F1 generation, the F2 generation, and each subsequent generation. The methods for screening such plants may employ a variety of statistical analyses and other methodologies for evaluating plants of each generation and designing a breeding program for cultivating new corn lines derived from the plants of the inbred corn line KCNI 330.

C. Transformation

Genetic transformation may also be used to develop plants of a corn line derived from the inbred corn line KCNI 330, including plants of a hybrid corn variety having the inbred corn line KCNI 330 as one of the parent lines. Genetic transformation refers to the introduction of foreign genes, or transgenes, into the genome of a plant. In some embodiments, methods for genetic transformation include particle bombardment, polyethylene glycol incubation, silica carbide whiskers, microinjection, macroinjection, microlaser, liposome, pollen tube pathway, electrophoresis, or *Agrobacterium*-mediated methods. (e.g., Wang et al., *Maize Transformation*, Handbook of Maize, Genetics and Genomics, (2009).) Genetic transformation may be used to generate plants with more useful phenotypes that would otherwise be unachievable by using natural plant breeding techniques and in a manner that can be more efficient than natural plant breeding.

Examples of desired traits that could be introduced into plants of the inbred corn line KCNI 330 or plants of a corn line derived from inbred corn line KCNI 330 through the use of genetic transformation include male sterility, herbicide resistance, insect resistance, bacterial disease resistance, fungal disease resistance, viral disease resistance, or the like.

Male Sterility:

As discussed, male sterility can be conferred on a corn plant through the use of many techniques, one of which is genetic transformation (e.g., Paul et al., *Plant Mol. Biol.* 19:611-22 (1992)). It may also be advantageous to restore male fertility in subsequent generations through the use of a male-fertility restorer gene.

Herbicide Resistance:

Herbicide resistance can be particularly useful for plants that are produced in large-scale agricultural operations. Plants can be genetically transformed with genes that confer resistance to herbicides that inhibit the growing point or meristem (e.g., Lee et al., *EMBO J.* 7:1241 (1998); Mild et al., *Theor. Appl. Genet.* 80:449 (1990)); resistance to herbicides with glyphosate and other phosphono compounds; resistance to herbicides with pyridinoxy or phenoxy propionic acids and cyclohexanes (e.g., Marshall et al., *Theor. Appl. Genet.* 83:435 (1992)); resistance to herbicides that inhibit photosynthesis (e.g., Przibilla et al., Plant Cell 3:169 (1991)); or the like.

Insect Resistance:

Plants can be genetically transformed to produce proteins and other compounds with insecticidal properties including, but not limited to: a *Bacillus thuringiensis* protein (e.g., Geiser et al., *Gene* 48:109 (1986)); insect-specific hormones or pheromones (e.g., Hammock et al., *Nature* 344:458 (1990)); insect-specific peptides (e.g., Regan, *J. Biol. Chem.* 269:9 (1994); Pratt et al., *Biochem. Biophys. Res. Comm.* 163:1243 (1989); Kramer et al., *Insect Biochem. Molec. Biol.* 23:691 (1993); Kawalleck et al., *Plant Molec. Biol.* 21:673 (1993)); insect-specific toxins; enzymes that encourage accumulation of compounds having insecticidal properties; insect-specific antibodies; or the like.

Bacterial Disease Resistance:

Plants can be genetically transformed to produce proteins and other compounds with antibacterial properties including, but not limited to: bacteria-specific peptides (e.g., Jaynes et al., *Plant Sci.* 89:43 (1993)); bacteria-specific toxins; activation of the Systemic Acquired Resistance response pathway (e.g., Ryals et al. *The Plant Cell,* 8:1809-19 (1996)); or the like.

Fungal Disease Resistance:

Plants can be genetically transformed to produce compounds with antifungal properties including, but not limited to: peptides with antifungal properties (e.g., Lamb et al., *Bio/Technology* 10:1436 (1992); Logemann et al., *Bio/Technology* 10:305 (1992)); antifungal genes (e.g., Cornelissen and Melchers, *Pl. Physiol.* 101:709-12 (1993); Parijs et al., *Planta,* 183:258-64 (1991); Bushnell et al., *Can. J. of Plant Path.* 20(2):137-49 (1998)); activation of the Systemic Acquired Resistance response pathway (e.g., Ryals et al. *The Plant Cell,* 8:1809-19 (1996)); or the like.

Viral Disease Resistance:

Plants can be genetically transformed to produce proteins and other compounds with antiviral properties including, but not limited to: a viral-invasive protein or toxin (e.g., Beachy et al. *Ann. Rev. Phytopathol.* 28:451 (1990)); antibodies (e.g., Tavladoraki et al. *Nature* 366:469 (1993)); activation of the Systemic Acquired Resistance response pathway (e.g., Ryals et al. *The Plant Cell,* 8:1809-19 (1996)); or the like.

Improved Agronomic Traits:

Plants can also be genetically transformed to exhibit improved agronomic traits, survive in hostile environments, or produce compounds desired for application in various industries. Examples include, but are not limited to: genes that help a plant survive in extreme temperatures, drought, or other harsh conditions; genes that cause modified fatty acid metabolism (e.g., Knultzon et al, *Proc. Natl. Acad. Sci. USA* 89:2624 (1992)); genes that cause modified carbohydrate composition (e.g., Pen et al., *Bio/Technol.* 10:292 (1992); Fisher et al., *Plant Physiol.* 102:1045 (1993)); genes that cause decreased phytate content (e.g., Van Hartingsveldt et al., *Gene* 127:87 (1993); Raboy et al, *Maydica* 35:383 (1990)); genes that cause increased production of antioxidants; or the like.

Additionally, a transgene may be introduced into plants of the inbred corn line KCNI 330 or plants of a corn line derived from inbred corn line KCNI 330 through a combination of genetic transformation and natural breeding techniques. In some embodiments, a plant of an inbred corn line having a transgene introduced into its genome may be crossed with a plant of the inbred corn line KCNI 330. This method introduces the transgene into plants of a subsequent generation that are derived from the plants of the inbred corn line KCNI 330.

D. Breeding Program Using Inbred Corn Line KCNI 330

The structuring of a breeding program using the inbred corn line KCNI 330 to create new inbred corn lines or hybrid corn varieties would be familiar to one of skill in the art. Such a breeding program would include selecting at least one other corn line to cross with the inbred corn line KCNI 330, usually based on the presence of the one or more desired trait(s) in the other corn line. In some embodiments, a person of ordinary skill may also determine if the other corn line that will be crossed with the inbred corn line KCNI 330 possess complementary genetics to the inbred corn line KCNI 330. The factors that may be considered when selecting other corn lines include floral synchronization (nicking), seed yields in female-designated inbred corn lines, pollen production capability of male-designated inbred corn lines, and responses of the plants of the inbred corn lines to fertility, pests, diseases, and pesticides. For more information concerning developing, cultivating, and selecting inbred corn lines for hybrid corn variety development see, e.g., Beck, Management of Hybrid Maize Seed Production (2002).

Once the plants are crossed, the progeny plants are evaluated to determine whether the desired trait(s) have been successfully transferred to the progeny plants. This may include taking observations after planting and growing the progeny plants or analyzing the genetic make-up of the progeny plants to determine if the gene or genes conferring the desired trait(s) have been successfully incorporated into the genome of the progeny plant.

A person of ordinary skill in the art may also use various techniques to ensure that the gene or genes conferring the desired trait have been successfully incorporated into the genome of the progeny plants. For example, PCR and Southern hybridization may be useful for confirming the presence of a given genetic locus (e.g., Sambrook et al., *Molecular Cloning* (2001); Shure et al, *Cell,* 35(1):225-33 (1983)). If the desired trait is conferred by a genetic locus that acts as a dominant trait, direct selection may be used. For example, if the desired trait is herbicide resistance, the progeny plants may be sprayed with the target herbicide. After the herbicide is applied to the progeny plants, it would be apparent which plants had the desired herbicide-resistance trait (those that survived) and which plants did not have the desired herbicide-resistance trait (those that were eliminated).

Alternatively, or in combination with other techniques, molecular markers may also be used to help in the selection of desired plants or crosses. Such markers may be identified through a variety of techniques, including but not limited to: Isozyme Electrophoresis or Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length Polymorphisms (AFLPs), Simple Sequence Repeats (SSRs), or Single Nucleotide Polymorphisms (SNPs). For further explanations of these techniques and examples for application, see e.g., Lee, M., "Inbred Lines of Maize and Their Molecular Markers" *The Maize Handbook,* 423-32 (1994); Smith et al, *Theoretical and Applied Genetics* 95:163-73 (1997); Pejic et al., *Theoretical and Applied Genetics* 1248-55 (1998); Boppenmaier, et al., *Maize Genetics Cooperative Newsletter,* 65:90 (1991). These markers may be used to identify alleles and confirm that those alleles are present in the progeny plants. The markers may also be used to select those progeny plants having the genome of the recurrent parent as opposed to the donor parent in a breeding program using a backcrossing technique. A person of skill in the art would be familiar with the use and various applications of molecular markers in a breeding program.

III. Tissue Cultures of Inbred Corn Line KCNI 330

In some embodiments, tissue cultures may also be used to develop and propagate plants of the inbred corn line KCNI 330. A tissue culture may include isolated cells of the same type or a different type or a collection of such cells organized into intact parts of a plant. In one embodiment, a small sample, known as an explant, is removed from a plant of the inbred corn line KCNI 330. The explant surface is then sterilized. The explant is placed on a nutrient medium and induced to undergo a process of dedifferentiation, after which it becomes a callus. The callus is then transferred to a different medium to induce shoot formation. After the shoots have formed, the tissue culture is then transferred to a rooting medium to complete plantlet regeneration. From this, a plant of the inbred corn line KCNI 330 may be generated from a tissue culture. The generated plant of the inbred corn line KCNI 330 may then be used in a breeding program to produce plants of the inbred corn line KCNI 330 or plants of a corn line derived from inbred corn line KCNI 330.

Tissue cultures may be generated from many different parts of the plant including, but not limited to: protoplasts, calli, meristematic cells, pollen, and intact cells such as embryos, pollen, flowers, kernels, leaves, ears, cobs, husks, stalks, roots, root tips, anthers, and silk. A person of skill in the art would be familiar with the various types of tissue cultures and the various methods for cultivating and using tissue cultures to regenerate and propagate plants. (See, e.g., Gaillard et al., *Plant Cell Reports,* 10(2):55 (1991); Green and Rhodes *Maize for Biol. Research,* 367-72 (1982); Duncan et al., *Planta,* 165:322-32 (1985); Songstad et al., *Plant Cell Reports,* 7:262-65 (1988); Rao et al., *Maize Genetics Cooperation Newsletter,* 60, (1986); Conger et al., *Plant Cell Reports,* 6:345-47 (1987); Armstrong and Green, *Planta,* 164:207-14 (1985); Gordon-Kamm et al., *The Plant Cell,* 2:603-18 (1990)).

It is noted that the terms "substantially" and "about" may be utilized herein to represent the inherent degree of uncertainty that may be attributed to any quantitative comparison, value, measurement, or other representation. These terms are also utilized herein to represent the degree by which a quantitative representation may vary from a stated reference without resulting in a change in the basic function of the subject matter at issue.

While particular embodiments have been illustrated and described herein, it should be understood that various other changes and modifications may be made without departing from the spirit and scope of the claimed subject matter. For example, certain agents that are both chemically and physiologically related or similar may be substituted for the agents described herein to achieve the same or similar results. All similar substitutes and modifications that would be apparent to one of skill in the art are within the spirit and scope of the claimed subject matter. Moreover, although various aspects of the claimed subject matter have been described herein, such aspects need not be utilized in combination. It is therefore intended that the appended claims cover all such changes and modifications that are within the scope of the claimed subject matter.

The references cited herein provide exemplary procedural details and other details that are supplementary to those set forth herein. Such references are specifically incorporated herein by reference.

What is claimed is:

1. A plant of inbred corn line KCNI 330, wherein a sample of seed of the plant of inbred corn line KCNI 330 has been deposited under ATCC Accession Number PTA-123287.

2. A plant part of the plant of inbred corn line KCNI 330 of claim 1.

3. The plant part of claim 2, wherein the plant part is a pollen grain, a protoplast, a cell, a tassel, an anther, or an ovule.

4. A tissue culture of regenerable cells produced from the plant of inbred corn line KCNI 330 of claim 1.

5. A plant regenerated from the tissue culture of claim 4 wherein the plant expresses all of the physiological and morphological characteristics of the plant of inbred corn line KCNI 330.

6. A plant that expresses all of the physiological and morphological characteristics of the plant of inbred corn line KCNI 330 of claim 1.

7. A hybrid plant, wherein at least one parent of the hybrid plant is the plant of inbred corn line KCNI 330 of claim 1.

8. The hybrid plant of claim 7, the hybrid plant expressing all of the physiological and morphological characteristics of the plant of inbred corn line KCNI 330 of claim 1.

9. The hybrid plant of claim 7, wherein the seed of the hybrid plant contains between 300 mg anthocyanins/kg dry corn and 400 mg anthocyanins/kg dry corn of total anthocyanins.

10. A seed of inbred corn line KCNI 330, wherein a sample of the seed of inbred corn line KCNI 330 has been deposited under ATCC Accession Number PTA-123287.

11. The seed of claim 10, wherein the seed contains between 500 mg anthocyanins/kg dry corn and 600 mg anthocyanins/kg dry corn of total anthocyanins.

12. A method of producing a plant derived from a plant of inbred corn line KCNI 330, wherein the method comprises crossing the plant of inbred corn line KCNI 330, of which a sample of seed has been deposited under ATCC Accession Number PTA-123287, with a plant of a different genotype to produce at least a first seed.

13. The method of claim 12, further comprising the steps of crossing a plant grown from the first seed with itself or a plant of a different genotype to produce a seed of a progeny plant; (b) growing the progeny plant from the seed of the progeny plant and crossing the progeny plant with itself or a plant of a different genotype; and (c) repeating steps (a) and (b) until a seed of a plant derived from the inbred corn line KCNI 330 is produced.

14. The method of claim 13, further comprising crossing the plant derived from inbred corn line KCNI 330 with a plant of a different genotype to produce seed of a hybrid plant derived from the inbred corn line KCNI 330.

15. The method of claim 12, wherein the first seed comprises between 300 mg anthocyanins/kg dry corn and 600 mg anthocyanins/kg dry corn of total anthocyanins.

16. The method of claim 15, wherein the first seed comprises between 500 mg anthocyanins/kg dry corn and 600 mg anthocyanins/kg dry corn of total anthocyanins.

17. The method of claim 12, wherein the plant of a different genotype comprises a desired trait.

18. The method of claim 17, wherein the desired trait is selected from the group consisting of male sterility, herbicide resistance, insect resistance, bacterial disease resistance, fungal disease resistance, and viral disease resistance.

19. The method of claim 17, further comprising the steps of (a) crossing a plant grown from the first seed with itself or a plant of a different genotype to produce progeny plants, wherein at least some of the progeny plants comprise the desired trait; (b) selecting the progeny plants that comprise the desired trait; (c) crossing the selected progeny plants with a plant of inbred corn line KCNI 330 to produce backcross progeny plants, wherein at least some of the backcross progeny plants comprise the desired trait; (d) selecting for the backcross progeny plants comprising the desired trait; and (e) repeating steps (c) and (d) until a seed of a plant derived from the inbred corn line KCNI 330 is produced, wherein the plant derived from the inbred corn line KCNI 330 comprises the desired trait.

20. The method of claim 19, wherein the seed of the plant derived from the inbred corn line KCNI 330 comprising the desired trait further comprises between 500 mg anthocyanins/kg dry corn and 600 mg anthocyanins/kg dry corn of total anthocyanins.

\* \* \* \* \*